(12) United States Patent
Kwak et al.

(10) Patent No.: US 8,124,796 B2
(45) Date of Patent: Feb. 28, 2012

(54) METHOD FOR PREPARING 3-HYDROXYTETRAHYDROFURAN USING CYCLODEHYDRATION

(75) Inventors: Byong Sung Kwak, Daejeon (KR); Tae Yun Kim, Daejeon (KR); Jin Woong Kim, Daejeon (KR); Sang Il Lee, Daejeon (KR); Ki Ho Koh, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 795 days.

(21) Appl. No.: 12/160,261

(22) PCT Filed: Jan. 10, 2006

(86) PCT No.: PCT/KR2006/000091
§ 371 (c)(1),
(2), (4) Date: Jul. 8, 2008

(87) PCT Pub. No.: WO2007/081065
PCT Pub. Date: Jul. 19, 2007

(65) Prior Publication Data
US 2009/0005581 A1 Jan. 1, 2009

(51) Int. Cl.
*C07D 307/02* (2006.01)

(52) U.S. Cl. .................. 549/475; 549/479

(58) Field of Classification Search .............. 549/475, 549/479
See application file for complete search history.

(56) References Cited

U.S. PATENT DOCUMENTS

| 4,539,415 A | 9/1985 | Mueller et al. |
| 5,780,649 A | 7/1998 | Yuasa et al. |

FOREIGN PATENT DOCUMENTS

EP 1 088 820 A1 4/2001

OTHER PUBLICATIONS

European Search Report dated Nov. 23, 2010 for the E.P. counterpart (EP 06700116.4, based on PCT/KR2006/000091) to the instant U.S. Appl. No. 12/160,261.
Tandon; J. Org. Chem. vol. 48, pp. 2767-2769 (1983).

*Primary Examiner* — Andrew D Kosar
*Assistant Examiner* — Raymond Covington
(74) *Attorney, Agent, or Firm* — McDermott Will & Emery LLP

(57) ABSTRACT

Disclosed is a method of preparing 3-hydroxytetrahydrofuran using cyclodehydration. More particularly, this invention relates to a method of preparing 3-hydroxytetrahydrofuran, including subjecting 1,2,4-butanetriol to cyclodehydration under reaction conditions of a reaction temperature of 30~180° C. and reaction pressure of 5000 psig or less in the presence of a strong acid cation exchange resin catalyst having a sulfonic acid group as an exchange group. According to the method of this invention, 3-hydroxytetrahydrofuran can be economically prepared at higher yield and productivity than when using conventional methods.

7 Claims, No Drawings

METHOD FOR PREPARING 3-HYDROXYTETRAHYDROFURAN USING CYCLODEHYDRATION

CROSS REFERENCE TO PRIOR APPLICATIONS

This application is the U.S. national phase of International Application No. PCT/KR2006/000091, filed Jan. 10, 2006. The disclosure of which is incorporated herein by reference in its entirety. The International Application published in English on Jul. 19, 2007 as WO 2007/081065 under PCT Article 21(2).

TECHNICAL FIELD

The present invention relates, in general, to a method of preparing 3-hydroxytetrahydrofuran using cyclodehydration, and, more particularly, to a method of preparing 3-hydroxytetrahydrofuran, comprising subjecting 1,2,4-butanetriol to cyclodehydration in the presence of a strong acid resin catalyst having a sulfonic acid group as an exchange group.

BACKGROUND ART

Generally, 3-hydroxytetrahydrofuran is useful as a chemical intermediate in the preparation of medicines and agricultural chemicals. Conventional techniques for preparing 3-hydroxytetrahydrofuran from 1,2,4-butanetriol are as follows.

In J. Org. Chem. 1983. Vol 48, 2767-2769 by Vishnu K. Tandon, a method of preparing (S)-3-hydroxytetrahydrofuran and (R)-3-hydroxytetrahydrofuran from (S)-1,2,4-butanetriol and (R)-1,2,4-butanetriol through cyclodehydration in the presence of para-toluenesulfonic acid as a catalyst was disclosed, the yield of the product being merely 87%.

U.S. Pat. No. 4,539,415 discloses a method of preparing racemic 3-hydroxytetrahydrofuran at a high yield through cyclodehydration in the presence of a fuller's earth catalyst. Although this method is suitable for the preparation of racemic 3-hydroxytetrahydrofuran through dehydration using a catalyst at a high temperature of 150-200° C., at which racemization may occur, it is limited in application to the process of preparing optically pure 3-hydroxytetrahydrofuran.

Therefore, the present invention aims to provide not only a method of preparing racemic 3-hydroxytetrahydrofuran at a high yield through cyclodehydration of butanetriol but also a method of preparing 3-hydroxytetrahydrofuran having high optical purity by maintaining the optical purity of butanetriol upon cyclodehydration.

DISCLOSURE

Technical Problem

Leading to the present invention, intensive and thorough research into the preparation of 3-hydroxytetrahydrofuran, carried out by the present inventors aiming to avoid the problems encountered in the related art, resulted in the discovery of a method of preparing 3-hydroxytetrahydrofuran at a high yield while maintaining the optical purity of 1,2,4-butanetriol in the presence of a strong acid ion exchange resin catalyst having a sulfonic acid group as an exchange group.

Accordingly, an object of the present invention is to provide a method of preparing 3-hydroxytetrahydrofuran from 1,2,4-butanetriol, capable of increasing the preparation yield and maintaining the optical purity of the reactant, compared to when using conventional methods.

Technical Solution

In order to accomplish the above object, the present invention provides a method of preparing 3-hydroxytetrahydrofuran using cyclodehydration, comprising subjecting 1,2,4-butanetriol having racemic or optical purity as a reactant to cyclodehydration under reaction conditions of a reaction temperature of 30-180° C. and reaction pressure of 5000 psig or less using a batch type or continuous fixed-bed reactor in the presence of a strong acid ion exchange resin catalyst, to thus obtain 3-hydroxytetrahydrofuran having racemic or optical purity equivalent to that of the reactant at a high yield.

Advantageous Effects

According to the present invention, 1,2,4-butanetriol is subjected to cyclodehydration under predetermined reaction conditions using a strong acid cation exchange resin catalyst having a sulfonic acid group as an exchange group, thereby economically preparing 3-hydroxytetrahydrofuran having optical purity equivalent to that of the reactant at a higher yield and higher productivity, compared to when using conventional methods.

BEST MODE

Hereinafter, a detailed description will be given of the present invention.

In the present invention, the method, in which 1,2,4-butanetriol is converted into 3-hydroxytetrahydrofuran at a high yield using a predetermined catalyst while maintaining the optical purity thereof is provided.

According to the present invention, 1,2,4-butanetriol having racemic or optical purity is subjected to cyclodehydration using a batch type or continuous fixed-bed reactor in the presence of a strong acid ion exchange resin as a catalyst, to thus obtain 3-hydroxytetrahydrofuran having racemic or optical purity equivalent thereto.

The cyclodehydration is schematically represented by Reaction 1 below:

Reaction 1

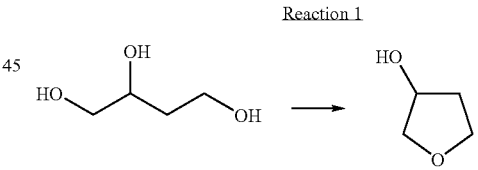

As is apparent from Reaction 1, the catalyst used in the cyclodehydration is a strong acid cation exchange resin having sulfonic acid (—SO$_3$H) as an exchange group, and is preferably a copolymer of styrene and divinylbenzene, in which a sulfonic acid group is contained as an exchange group.

In the present invention, when the cyclodehydration is conducted in the presence of the strong acid ion exchange resin catalyst having a sulfonic acid group as an exchange group, this reaction may be carried out in a batch type process or a continuous process. In particular, a continuous process using a continuous fixed-bed reactor is preferable in the interest of productivity.

As such, the cyclodehydration is conducted at a reaction temperature of 30-180° C., and preferably 50-150° C. When the reaction temperature is lower than 30° C., little reaction activity is exhibited. On the other hand, when the reaction temperature exceeds 180° C., it is difficult to maintain reaction selectivity and to assure optical purity equivalent to that of the reactant.

Further, although the reaction pressure is not limited, it falls within a range of 5000 psig or less, and preferably 1500 psig or less, in order to be suitable for a commercial process.

In the case where the cyclodehydration is conducted using a fixed bed reaction system, a weight hourly space velocity (WHSV) is 0.1-30 $h^{-1}$, and preferably 0.2-20 $h^{-1}$. When the WHSV is less than 0.1 $h^{-1}$, productivity is decreased. On the other hand, when the WHSV exceeds 30 $h^{-1}$, reaction activity is reduced.

Further, air or inert gas may be fed into the fixed-bed reactor in order to increase reactivity. In this case, the amount of gas to be used is not limited, but the use of gas which does not react with the reactant or the product is preferable.

In addition, upon cyclodehydration, a solvent may be used, in addition to 1,2,4-butanetriol as the reactant. Although the solvent used in the present invention is not particularly limited, a solvent which is easy to separate from the product is useful. For example, a nonpolar organic solvent, such as benzene, toluene, xylene, cyclohexane, hexane, or methylene chloride, or a polar solvent, including ether, such as diglyme, tetrahydrofuran, or dioxane, and including alcohol, such as ethanol, propanol, or polyethyleneglycol, may be used. Of these solvents, a polar solvent, including ether, such as diglyme, tetrahydrofuran, or dioxane, and alcohol, such as ethanol, propanol, or polyethyleneglycol, is preferably used. Further, it is possible to use a mixture of hydrocarbons.

Mode for Invention

A better understanding of the present invention may be obtained through the following comparative examples and examples, which are set forth to illustrate, but are not to be construed as the limit of the present invention.

Comparative Example 1

304 g of racemic 1,2,4-butanetriol, 304 g of polyethyleneglycol (Average MW=400 g/mol, hereinafter referred to as 'PEG-400'), and 41.6 g of para-toluenesulfonic acid were fed into a batch type reactor equipped with a distilling apparatus and then stirred. While the reaction pressure was reduced to 10 torr or less, and the temperature of the reactor was slowly increased to 120° C., the reaction was conducted for 12 hours. During the reaction, tetrahydrofuran was distilled and separated using the distilling apparatus provided at the upper portion of the reactor, thus yielding tetrahydrofuran having 98% or more purity at a yield of 85 mol %.

Comparative Examples 2-3

(S)-butanetriol having optical purity of 99.9% was allowed to react in a manner similar to that of Comparative Example 1, thus preparing (S)-3-tetrahydrofuran. The results of the experiment depending on the reaction temperature are shown in Table 1 below.

TABLE 1

|  | Reaction Temp. (° C.) | Yield (mol %) | Optical Purity (%) |
|---|---|---|---|
| C. Ex. 2 | 120 | 85 | 99.8 |
| C. Ex. 3 | 160 | 83 | 98.2 |

The optical purity was decreased under conditions of high reaction temperatures.

Example 1

Instead of PEG-400 and the para-toluenesulfonic acid catalyst used in Comparative Example 1, dioxane and a strong acid ion exchange resin (Amberlyst 15, $H^+$ form) containing a sulfonic acid group were used in equal amounts. Then, the reaction was conducted using a batch type reactor under conditions of atmospheric pressure and 100° C. for 20 hours. The reaction yield was 96 mol %.

Examples 2-3

5 g of the catalyst used in Example 1 was loaded into a completely automated continuous fixed-bed reactor made of 316 stainless steel, after which the internal temperature of the reactor was adjusted to 100° C., and then a dioxane solution containing 10 wt % of (S)-1,2,4-butanetriol (optical purity of 99.9%) was fed into the reactor at a WHSV of 2.0 $h^{-1}$ to thus conduct the reaction.

The results of the preparation of (S)-3-tetrahydrofuran are shown in Table 2 below.

TABLE 2

|  | Reaction Temp. (° C.) | Reaction Press. (psig) | Reaction Yield (mol %) | Optical Purity (%) |
|---|---|---|---|---|
| Ex. 2 | 100 | Atmosph. Pressure | 99 | 99.9 |
| Ex. 3 | 120 | 100 | 98 | 99.8 |

Example 4

5 g of the catalyst used in Example 1 was loaded into a completely automated continuous fixed-bed reactor made of 316 stainless steel, after which the internal temperature of the reactor was adjusted to 100° C. and then a dioxane solution containing 10 wt % of (R)-1,2,4-butanetriol (optical purity of 99.0%) was fed into the reactor at a WHSV of 2.0 $h^{-1}$ to thus conduct the reaction.

The results of the preparation of (R)-3-tetrahydrofuran are shown in Table 3 below.

TABLE 3

|  | Reaction Temp. (° C.) | Reaction Press (psig) | Reaction Yield (mol %) | Optical Purity (%) |
|---|---|---|---|---|
| Ex. 4 | 100 | Atmosph. Pressure | 99 | 99.0 |

Examples 5-6

5 g of the catalyst used in Example 1 was loaded into a completely automated continuous fixed-bed reactor made of 316 stainless steel, after which the internal temperature of the reactor was adjusted to 90° C., and then a dioxane solution containing 10 wt % of (S)-1,2,4-butanetriol (optical purity of 99.9%) was fed into the reactor at a WHSV of 2.0 $h^{-1}$ to thus conduct the reaction. Under these conditions, variation in the reaction activity depending on whether $N_2$ was added or not was observed.

The results of preparation of (S)-3-tetrahydrofuran are shown in Table 4 below.

TABLE 4

|  | Addition of $N_2$ | Reaction Press. (psig) | Reaction Yield (mol %) | Optical Purity (%) |
|---|---|---|---|---|
| Ex. 5 | 0 | Atmosph. Pressure | 70 | 99.9 |
| Ex. 6 | 6 cc/min | Atmosph. Pressure | 81 | 99.9 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing 3-hydroxytetrahydrofuran using cyclodehydration, comprising subjecting 1,2,4-butanetriol to cyclodehydration at a reaction temperature of 50-150° C. and reaction pressure of 5000 psig or less using a batch type or continuous fixed-bed reactor in the presence of a strong acid ion exchange resin catalyst, to thus obtain 3-hydroxytetrahydrofuran.

2. The method according to claim 1, wherein the acid ion exchange resin has a sulfonic acid group (—$SO_3H$) as an exchange group.

3. The method according to claim 2, wherein the acid ion exchange resin is a copolymer of styrene and divinylbenzene.

4. The method according to claim 1, wherein the reaction pressure is 1500 psig or less.

5. The method according to claim 1, wherein weight hourly space velocity is 0.1-30 $h^{-1}$ when the cyclodehydration is conducted in a continuous fixed-bed reactor.

6. The method according to claim 5, wherein the weight hourly space velocity is 0.2-20 $h^{-1}$.

7. The method of claim 1, wherein an optically pure 1,2,4-butanetriol is used and the 3-hydroxytetrahydrofuran obtained is optically pure.

* * * * *